United States Patent
Hu et al.

(10) Patent No.: US 9,936,923 B2
(45) Date of Patent: *Apr. 10, 2018

(54) SYSTEM AND METHODS FOR GENERATING PREDICTIVE COMBINATIONS OF HOSPITAL MONITOR ALARMS

(71) Applicant: THE REGENTS OF THE UNIVERSITY OF CALIFORNIA, Oakland, CA (US)

(72) Inventors: Xiao Hu, San Francisco, CA (US); Neil A. Martin, Encino, CA (US)

(73) Assignee: THE REGENTS OF THE UNIVERSITY OF CALIFORNIA, Oakland, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 15/426,859

(22) Filed: Feb. 7, 2017

(65) Prior Publication Data
US 2017/0209104 A1   Jul. 27, 2017

Related U.S. Application Data

(63) Continuation of application No. 14/228,549, filed on Mar. 28, 2014, now Pat. No. 9,600,990, which is a
(Continued)

(51) Int. Cl.
G08B 21/02 (2006.01)
A61B 5/00 (2006.01)
G08B 21/04 (2006.01)

(52) U.S. Cl.
CPC ......... *A61B 5/746* (2013.01); *G08B 21/0453* (2013.01)

(58) Field of Classification Search
CPC ...... A06F 19/30; A06F 19/32; A06F 19/3406; A06F 19/345; G08B 21/0438;
(Continued)

(56) References Cited

U.S. PATENT DOCUMENTS 6,585,645 B2   7/2003   Hutchinson
6,822,564 B2   11/2004   Al-Ali
(Continued)

FOREIGN PATENT DOCUMENTS

GB   2449347 A   11/2008
KR   1020030066322 A   8/2003

OTHER PUBLICATIONS

European Patent Office (EPO), Supplementary European Search Report dated Aug. 26, 2016, related European Patent Application No. 12839741.1, pp. 1-10, with claims searched, pp. 11-13.
(Continued)

*Primary Examiner* — Van Trieu
(74) *Attorney, Agent, or Firm* — O'Banion & Ritchey LLP; John P. O'Banion

(57) ABSTRACT

Systems and methods are disclosed for monitoring data associated with a plurality of physiological characteristics of a patient, comprising: the methods include generating a set of super-alarm patterns associated with the plurality of physiological conditions, wherein the super-alarm patterns comprising data relating to a combination of at least two individual raw alarms from independent physiological data streams that co-occur within a temporal window, and triggering an alarm if a combination of the input physiological data matches at least a portion of a generated super-alarm pattern.

23 Claims, 10 Drawing Sheets

Related U.S. Application Data continuation of application No. PCT/US2012/060135, filed on Oct. 12, 2012.

(60) Provisional application No. 61/547,022, filed on Oct. 13, 2011.

(58) Field of Classification Search
CPC .. G08B 21/0453; G08B 21/18; G08B 21/182; A61B 5/00; A61B 5/7271; A61B 5/7282; A61B 5/74; A61B 5/746; A61B 5/7275
See application file for complete search history.

(56) References Cited

U.S. PATENT DOCUMENTS

| | | |
|---|---|---|
| 8,374,988 B2 | 2/2013 | Gawlick |
| 8,416,085 B2 | 4/2013 | Gawlick |
| 8,417,662 B2 | 4/2013 | Gawlick |
| 8,591,455 B2 | 11/2013 | Mensinger |
| 9,095,316 B2 | 8/2015 | Welch |
| 2002/0177755 A1 | 11/2002 | Hutchinson |
| 2006/0074369 A1* | 4/2006 | Oishi ................ A61B 5/02152 604/4.01 |
| 2008/0157980 A1 | 7/2008 | Sachanandani |
| 2008/0300471 A1 | 12/2008 | Al-Ali |
| 2009/0240193 A1 | 9/2009 | Mensinger |
| 2010/0260325 A1 | 10/2010 | Clawson |
| 2011/0118573 A1 | 5/2011 | McKenna |
| 2011/0137134 A1 | 6/2011 | Hemmerling |
| 2011/0202495 A1 | 8/2011 | Gawlick |
| 2012/0286955 A1 | 11/2012 | Welch |

OTHER PUBLICATIONS

Korean Intellectual Property Office (KIPO), International Search Report and Written Opinion, dated Mar. 18, 2013, for corresponding PCT International Application No. PCT/US2012/060135 (pp. 1-10) with claims searched (pp. 11-17).

* cited by examiner

SYSTEM AND METHODS FOR GENERATING PREDICTIVE COMBINATIONS OF HOSPITAL MONITOR ALARMS

CROSS-REFERENCE TO RELATED APPLICATIONS

This application is a continuation of U.S. patent application Ser. No. 14/228,549 filed on Nov. 7, 2016, incorporated herein by reference in its entirety, now U.S. Pat. No. 9,600,990, which is a 35 U.S.C. § 111(a) continuation of PCT international application number PCT/US2012/060135 filed on Oct. 12, 2012, incorporated herein by reference in its entirety, which claims priority to, and the benefit of, U.S. provisional patent application Ser. No. 61/547,022 filed on Oct. 13, 2011, incorporated herein by reference in its entirety. Priority is claimed to each of the foregoing applications.

The above-referenced PCT international application was published as PCT International Publication No. WO 2013/056180 on Apr. 18, 2013, incorporated herein by reference in its entirety.

STATEMENT REGARDING FEDERALLY SPONSORED RESEARCH OR DEVELOPMENT

Not Applicable

INCORPORATION-BY-REFERENCE OF MATERIAL SUBMITTED IN A COMPUTER PROGRAM APPENDIX

Not Applicable

NOTICE OF MATERIAL SUBJECT TO COPYRIGHT PROTECTION

A portion of the material in this patent document is subject to copyright protection under the copyright laws of the United States and of other countries. The owner of the copyright rights has no objection to the facsimile reproduction by anyone of the patent document or the patent disclosure, as it appears in the United States Patent and Trademark Office publicly available file or records, but otherwise reserves all copyright rights whatsoever. The copyright owner does not hereby waive any of its rights to have this patent document maintained in secrecy, including without limitation its rights pursuant to 37 C.F.R. § 1.14.

BACKGROUND OF THE INVENTION

1. Field of the Invention

This invention pertains generally to monitor alarms, and more particularly to a bedside monitor for hospitals.

2. Description of Related Art

Bedside monitors are ubiquitous in acute care units of modern hospitals. However, they are often criticized for generating an excessive number of false positive and false alarms. Frequent false positive alarms not only create annoying distractions but also can cause alarm fatigue for bedside care givers so that attentions to critical alarms are missed raising serious patient safety concerns. Indeed, recent mainstream reports have published cases of avoidable patient deaths that were unfortunately related to the alarm fatigue/desensitization among bedside care givers. Therefore, it is imperative to investigate different strategies to improve patient monitor alarm generation and management.

The issue of false alarms and false positive alarms has been well studied. In a recent report, only 15% of alarms have been found to be clinically relevant in a medical intensive care unit (ICU). In an emergency room setting, it has been reported that only 0.7% of alarms are true positives meaning that they have detected adverse events and led to clinical interventions. Similar findings regarding a high percentage of clinically irrelevant alarms have been reported in diverse ICU environments. False positive alarms can be caused either by false alarms due to noise and artifacts in signals or by inappropriate alarming criteria that are too generic and sensitive. Indeed, most of the threshold-based alarms despite being true alarms are false positives. Extensive research efforts have been put into developing solutions to reduce the false positive rate of monitor alarms. Understandably, the majority of these efforts have been targeted at improving signal processing aspects of alarm generation with the hope that robust signal processing can lead to fewer false alarms. Reducing the false positive rate beyond reducing the number of false alarms is more challenging because of the need for highly sensitive monitoring in an acute care setting.

A direct analysis of alarms has been undertaken in existing studies but the focus has been on annotating individual alarms by trained observers to categorize them into false and true positive alarms. This effort indeed matches the prevailing patient monitoring practice where care givers process alarms one by one as they go off. Little time is available for them to recall historical alarms and then manually associate them with the current alarm to create a more holistic assessment of patients.

Accordingly, an object of the present invention is the ability to account for potential predictive patterns arising from a combination of different single alarms.

BRIEF SUMMARY OF THE INVENTION

An aspect of the present invention is a method that is capable of mining a collection of monitor alarms to search for frequent but also specific combinations of encoded monitor alarms to predict certain adverse event, such as in-hospital code blue arrests or other target events.

Another aspect is an alarm data mining method to extract patterns formed as alarm combinations that are predictive of code blue events. The method of the present invention leverages itemset mining and information metric based discretization methods.

Further aspects of the invention will be brought out in the following portions of the specification, wherein the detailed description is for the purpose of fully disclosing preferred embodiments of the invention without placing limitations thereon.

BRIEF DESCRIPTION OF THE SEVERAL VIEWS OF THE DRAWING(S)

The invention will be more fully understood by reference to the following drawings which are for illustrative purposes only:

DETAILED DESCRIPTION OF THE INVENTION

Figure 1A:
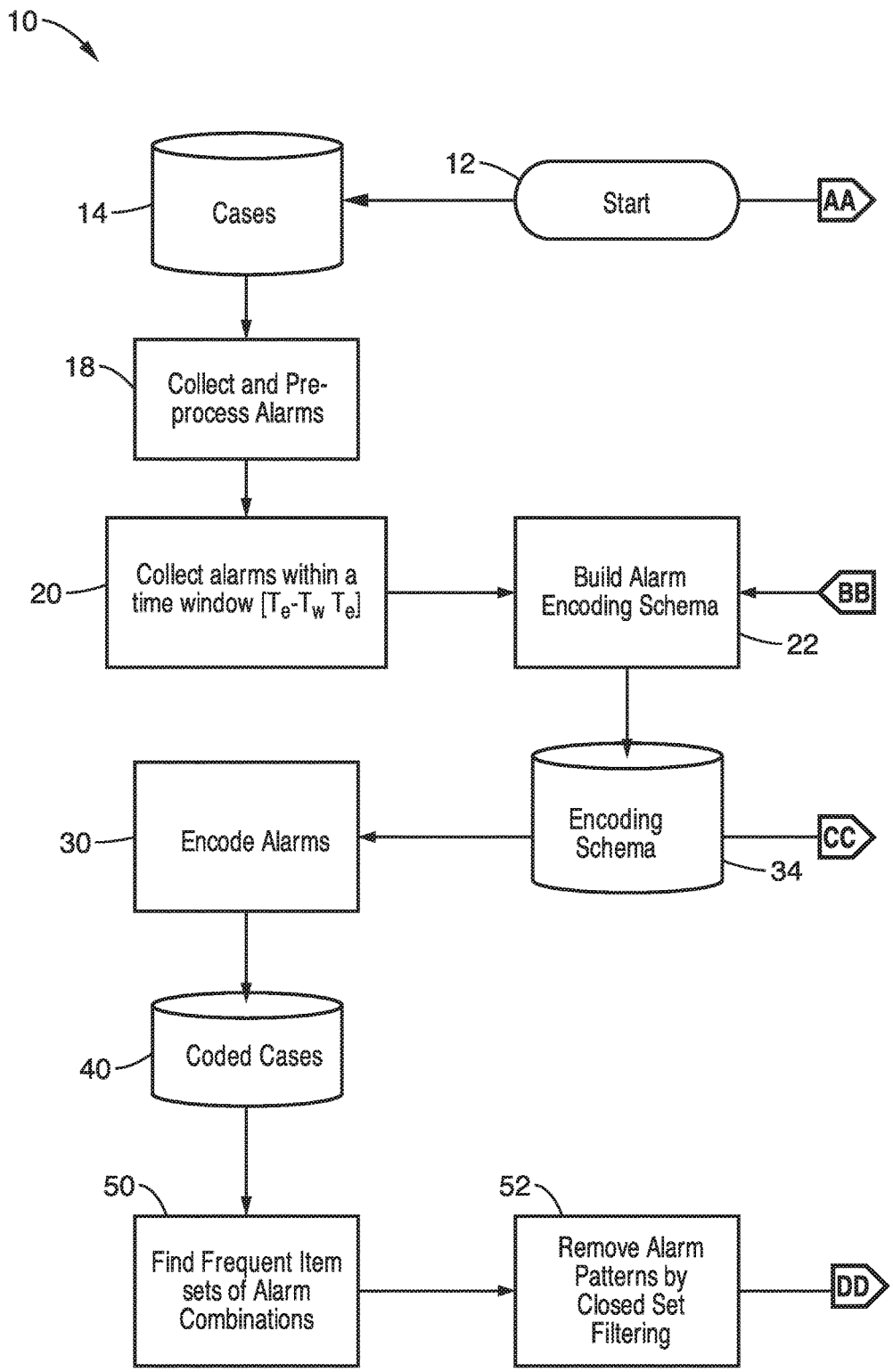
FIGS. 1A and 1B show a flowchart of the alarm data mining method to generate a set of super-alarm patterns in accordance with the present invention.
Figure 1B:
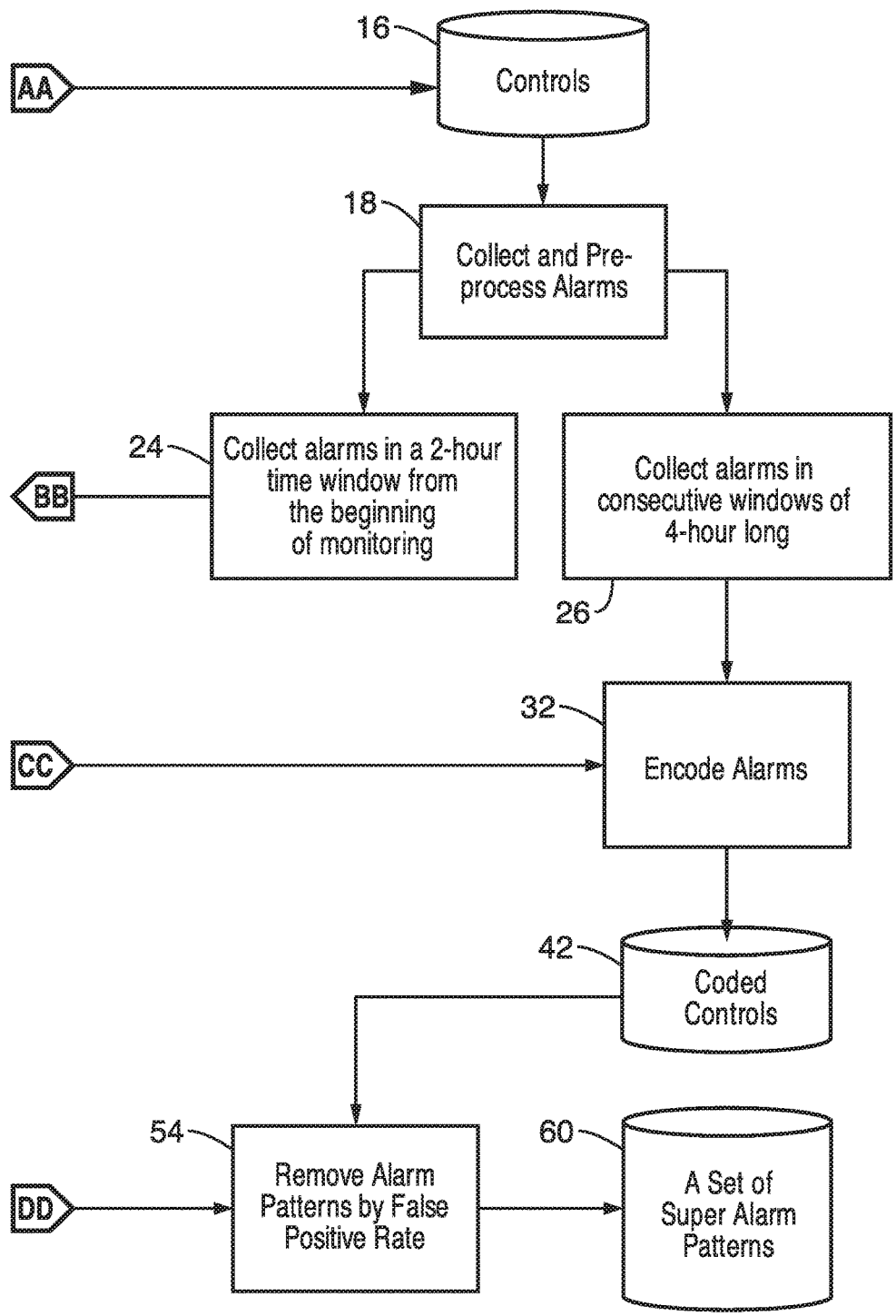

FIGS. 1A and 1B show a flow diagram of an alarm data mining method 10 to generate a set of super-alarm patterns 60 in accordance with the present invention. For purposes of the following description, a combination of individual encoded raw alarms that co-occur within a temporal window is termed a super-alarm pattern. The goal of method 10 is to construct a set of predictive super-alarm patterns 60 from two collections 14, 16 of raw alarm data, which may be stored in a database or like memory allocation.

As shown in FIG. 1A, the first collection (cases 14) includes alarms that precede code blue events in multiple patients. While code blue events were chosen as the endpoint for purposes of this description, it is appreciated that any event may be used. Table 1 shows the typical composition of monitor alarms by using four examples. A raw monitor alarm will often include a unique alarm code assigned by the monitor manufacturer, a textual label of the alarm which is often uniquely mapped to the alarm code, an optional polarity indicator that denotes whether a parametric alarm exceeds an upper bound (HI) or a lower bound (LO) threshold, an optional value at which the preset alarm thresholds have been crossed to trigger this alarm, and the timestamp when this alarm occurs. There are four built-in levels of alarms as determined by bedside monitors, which are usually set up by a unit-based policy. These four levels are: crisis alarm, patient advisory alarm, patient warning alarm, and system warning alarm.

As shown in FIG. 1B, the second collection (controls 16) includes alarms from a set of control patients that are not coded.

Referring to both FIGS. 1A and 1B, the two collections 14 and 16 go through two different simultaneous branches of processing at starting point 12. The case data 14 are used to find super-alarm patterns occurring frequently within a window $T_w$ having a length of time that immediately precedes code blue events. The control data 16 are used to filter out those super-alarm patterns identified for code blue patients that have also occurred frequently for control patients. This is achieved by sampling alarms for control patients 16 in consecutive windows of n-hour long starting from the beginning of the monitoring to the end (see step 26 in FIG. 1B). Thus, alarm samples are assumed to be representative of the whole course of patient monitoring. Within each window, alarms are sampled from a randomly placed segment of length $T_w$. In this way, a false positive rate can be readily computed for each super-alarm pattern during the training phase. The method 10 also discretizes the value field for parametric alarms via the supply of both case 14 and control data 16. Hence, alarms within the first two hours of monitoring are used to generate the discretization schema.

Both the case data 14 and control data 16 first undergo a pre-processing step 18. Due to the fact that a bedside monitor can have multiple input ports to accommodate multiple monitoring modalities, the same device can be plugged into any of those ports and results in different labeling of the same alarm. In the example shown in Table 1, the arterial line (A-line) was plugged into port #1 and hence ART1 is part of the label. Thus pre-processing is performed to make each alarm agnostic to the specified port number. Also, alarms from noninvasive devices are treated as equivalent to those from its invasive counterpart, and hence alarms from invasive and noninvasive readings (e.g. blood pressure) are merged. Since the value of a measurement that triggers an alarm can be good indicator of the severity of the alarm, a discretization algorithm is employed to further divide a given alarm with a value field into sub-codes. This is referred to as "regular alarm encoding." A data-driven approach such as class-attribute contingency coefficient (CACC) may be used for discretization. This approach uses both case data and control data to create a two-class discrimination problem to find the optimal discretization that will result in the best correlation between individual attribute and classes. Thus, the collection of raw alarms 14, 16 that co-occur within a specified time window are pre-processed to generate an output of an array of alarm codes, each of which identifies an individual raw alarm.

Referring to FIG. 1A, after preprocessing, alarms within a time window $[T_e-T_w, T_e]$ are collected from the pre-processed case data 14 at step 20, where $T_e$ is the time of the event occurrence. These collected alarms are then used to build alarm encoding schema at step 22. Furthermore, control alarms collected within the first two hours of monitoring in step 24 are used to generate discretization schema in step 22.

Figure 2:
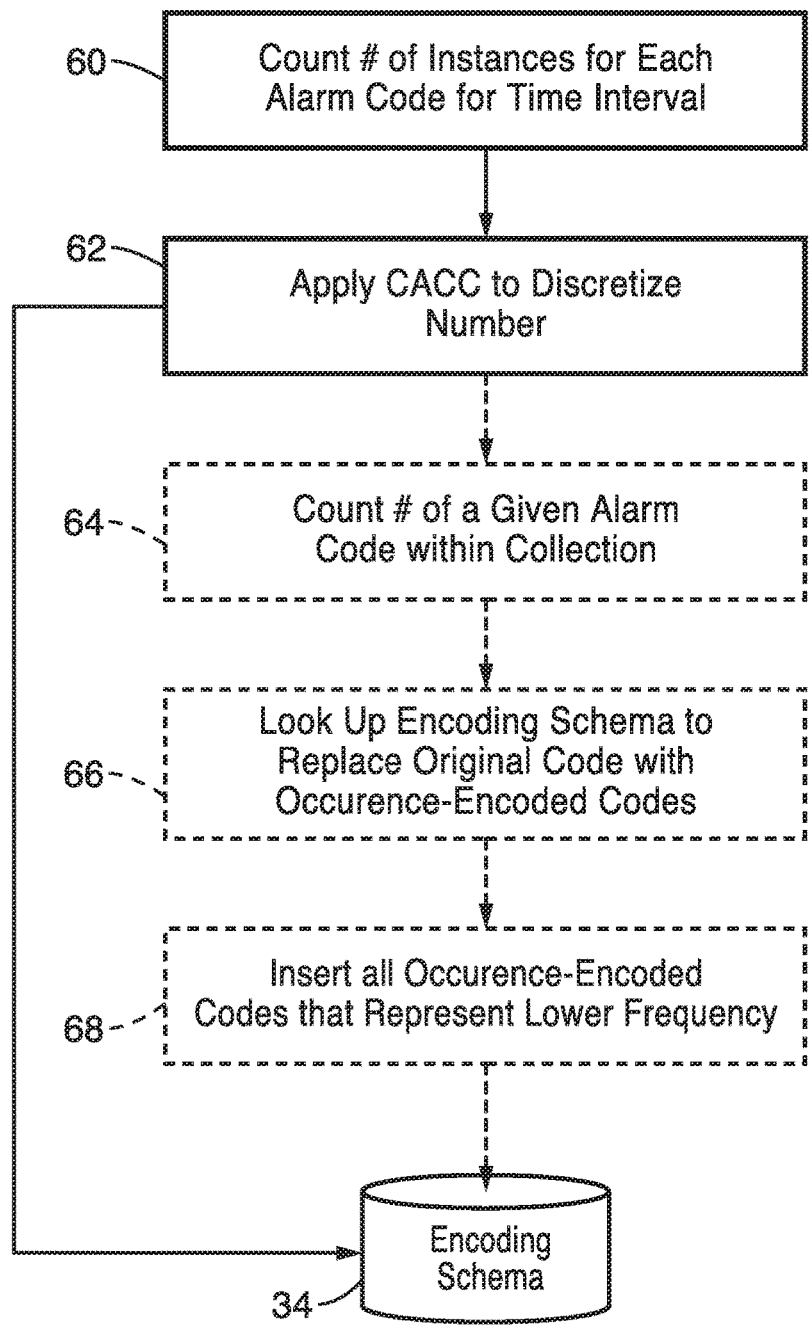
FIG. 2 is a flow diagram of the alarm encoding schema building step of the method of FIG. 1.

FIG. 2 illustrates the alarm encoding schema building step 22 in further detail. At step 60, the method counts the number of instances for each alarm code as encoded by the regular encoding process per patient within the selected time interval. The CACC algorithm is again applied at step 62 (in addition to preprocessing at step 18) to discretize this number to generate an expanded set of codes per each alarm code for encoding schema 34. A potentially important kind of information missing from the above regular encoding is the number of repetitions of a particular alarm within the given time window. An additional alarm encoding process may optionally be employed after regular encoding to account for the occurrence frequency for each alarm code. The number of a given alarm code within the collection is counted at step 64. Next, the method at step 66 looks up the encoding schema based on the obtained count to replace the original alarm code with the corresponding occurrence-encoded codes for this alarm code. Finally, all occurrence-encoded codes that represent the occurrence frequency lower than that of the current alarm are inserted at step 68. For example, if an alarm has occurred five times within a specified time period, and there are three levels of discretization for this alarm (e.g. first range of (0,2], second range of (2,4], and third range of (4,∞]), then an instance of this alarm having occurred five times would automatically imply that it is greater than 0 as well as greater than 2. Therefore, step 66 would insert the codes that correspond to first range (0,2] and second range (2,4].

The generated encoding schema 34 are then used to encode case alarms at step 30 to generate coded cases 40 (see FIG. 1A), and also encode control alarms at step 32 to generate coded controls 42 (see FIG. 1B).

Figure 3:
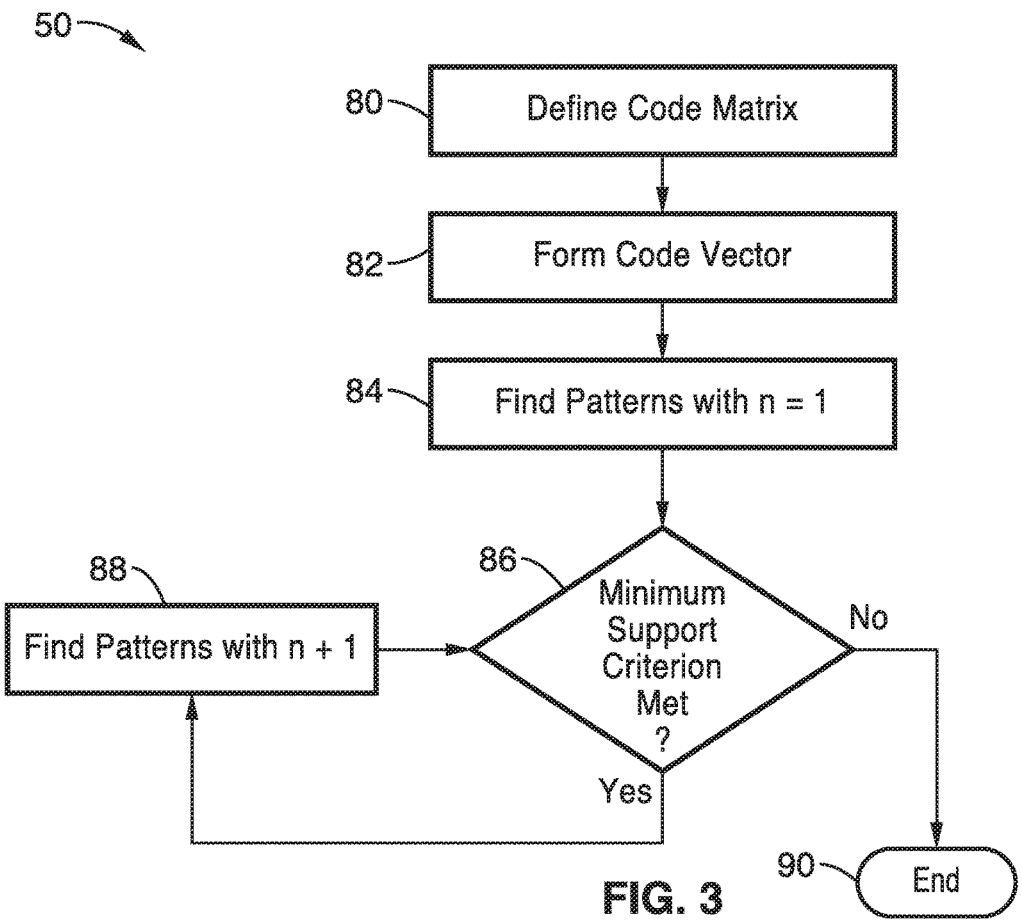
FIG. 3 is a flow diagram of the frequent alarm combination finding step of the method of FIG. 1.

Referring back to FIG. 1A, the coded cases 40 are used to find frequent itemsets of alarm combinations at step 50. Step 50 is further detailed in FIG. 3. The method of step 50 generally follows classic association rule mining algorithm by using the Apriori algorithm. However, it is appreciated that other rule mining algorithms known in the art may also be implemented. At step 80, a code matrix is defined according to Eq. 1:

$$C=[c_{i,j}]_{N_p \times N_c},\qquad\text{Eq. 1}$$

where $c_{ij}$ is zero if the $j^{th}$ alarm code (or its occurrence-encoded codes) for patient i is not present, and is one if this alarm code is present, $N_p$ and $N_c$ are number of patients and number of unique encoded alarm codes, respectively. At step 82, super-alarm pattern candidates that have only one alarm code to form a probe vector of Eq. 2:

$$\text{Probe}=[c_i]_{N_c \times 1},\qquad\text{Eq. 2}$$

where $c_i$ is zero if the $i^{th}$ alarm code is not present in this super-alarm pattern candidate. Testing whether a given super-alarm pattern candidate is frequent among code blue patients, the cardinality n (the number of elements in a set) for a given code matrix can be first calculated as C×Probe. For patients whose alarms contain all the codes in Probe, this multiplication will result in a number equal to the number of alarm code in the Probe. Frequent alarm combinations are then defined as those which are present in at least certain percentage of the patients in the training dataset, which is denoted as the minimum support threshold. After finding the super-alarm patterns with n=1 (e.g. one individual alarm) at step 84, the algorithm determines if the minimum support threshold is met at step 86. If yes, it then proceeds to form potential candidates with n=2 (combination of two alarms) at step 88. These candidates have to be formed from the alarm codes that have passed the support test when n=1 (greater than minimum support threshold). Then each candidate will form a Probe vector and be evaluated by a straight forward matrix multiplication C×Probe. This process is repeated by increasing the cardinality n of super-alarm pattern until no more patterns meet the minimum support criterion at step 90.

One heuristic to control the size of the super-alarm set, and hence potentially avoid false positive super-alarm patterns, is to remove those patterns that are included as part of longer patterns at step 52 with a hope to gain specificity without compromising sensitivity. In particular, let:

$$A^m=\{a_1,a_2,\ldots,a_m\}\qquad\text{Eq. 3}$$

and $$B^n=\{b_1,b_2,\ldots,b_n\}\qquad\text{Eq. 4}$$

where n<m, and $A^m$ is a super-alarm pattern that has been retained, and $B^n$ as a candidate pattern to be filtered out if the following conditions are both met:

1) Given any $b_i$, i=1,L,n, an $a_j$, j=1,L,m can be found to be equal to $b_i$.
2) There are no patients in the training data who have triggered but not.

Note, the above definition for filtering super-alarms within step 52 is may be referred to closed itemset mining, a special form of association rule mining.

Finally, data from the coded controls 42 (see FIG. 1B) is used to remove alarm patterns by false positive rate at step 54 to generate the set of super alarm patterns 60. A super-alarm pattern is excluded from the final super-alarm set 60 if this pattern's false positive rate (FPR), as evaluated using the training data, is greater than a predetermined threshold. FPR is calculated as the percentage of length windows from control patients 16 in the training data set that trigger this pattern.

Figure 4:
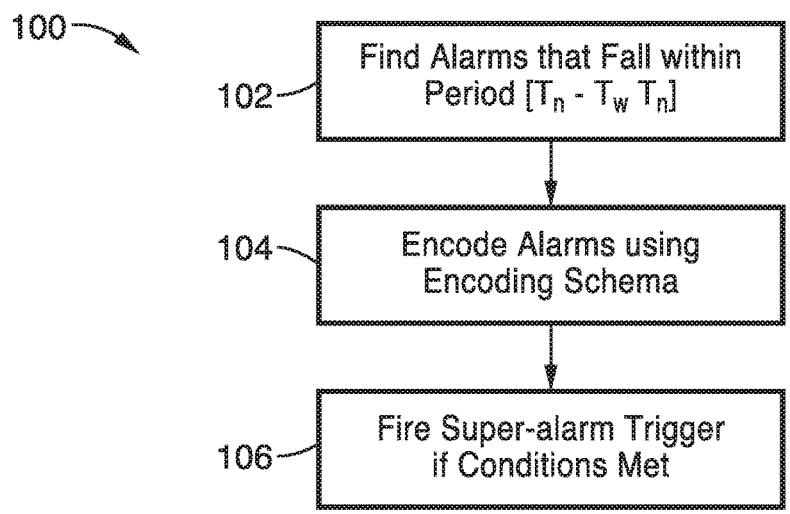
FIG. 4 is a flow diagram of the online operation method of the present invention.

Referring now to FIG. 4, an online operation method 100 using super-alarm patterns of the present invention is shown. To operate a super-alarm set in an online fashion, it is assumed that any new regular monitor alarm will trigger the evaluation of super-alarm set by the following steps.

Based on the time ($T_n$) of a new monitor alarm, the alarms that fall within the period $[T_n-T_w, T_n]$ are found at step 102, where $T_w$ is the length of the time window as used in finding the frequent combinations of regular alarms.

At step 104, these alarms are encoded using the coding schema 60 generated in the training phase 10.

At step 106, a super-alarm trigger is then fired if either the following conditions are both met:

1) any combination of encoded alarms is part of the patterns in the super-alarm set, or
2) The new alarms added at $T_n$ are part of at least one matched super-alarm pattern. This condition is used to avoid repeatedly triggering of a super-alarm solely based on the previous alarms.

Given a sequence of alarms from a patient, the above steps are executed sequentially for all the qualified regular monitor alarms (system warning alarms are not used) and thus simulate how a super-alarm set would be used in real-time.

Figure 5:
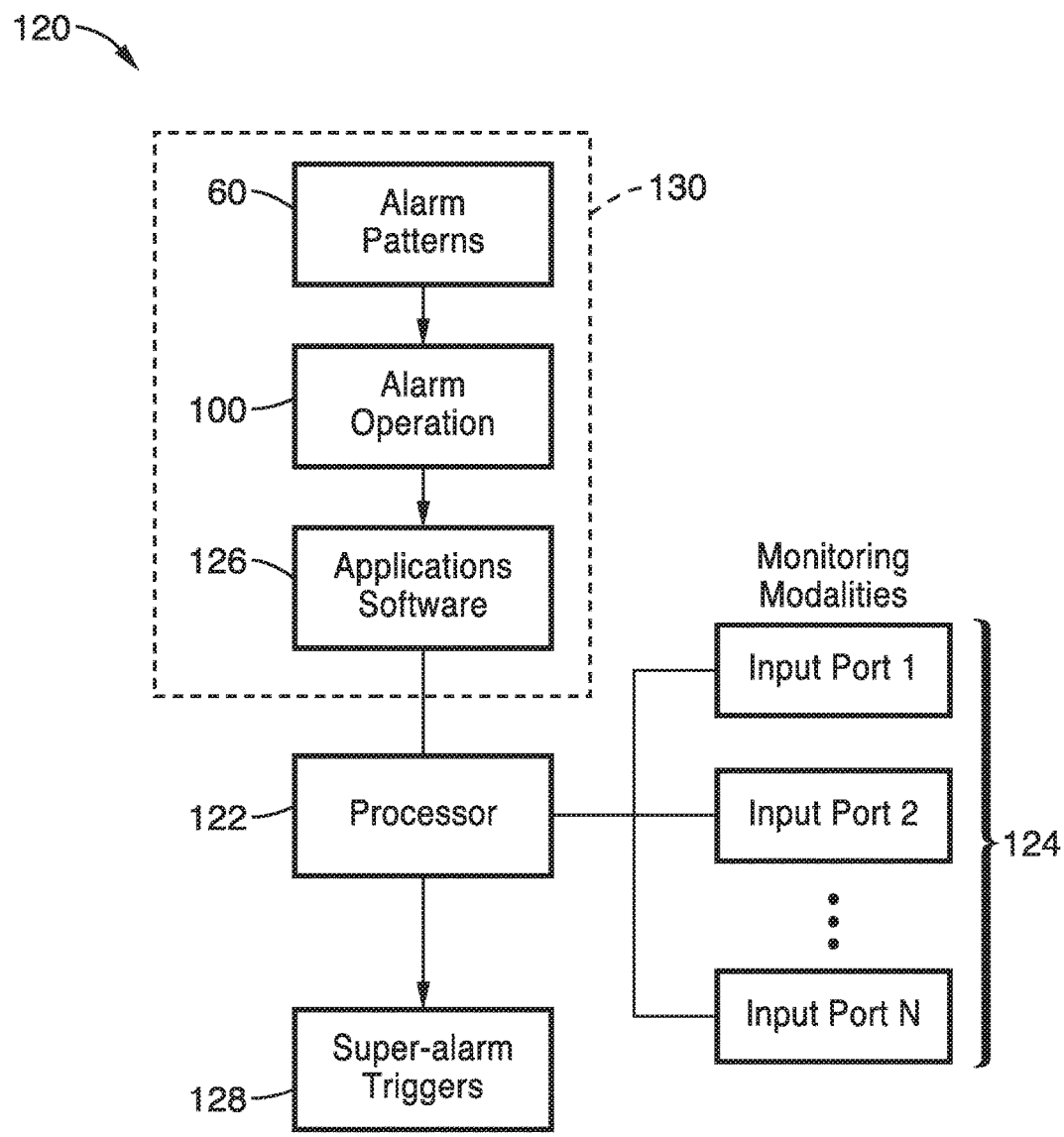
FIG. 5 is schematic diagram of a monitoring system incorporating the methods of FIGS. 1A through 5 in accordance with the present invention.

FIG. 5 illustrates an exemplary monitoring system 130 incorporating the super-alarm patterns 60 and operation method 100 described above as an application software 126. Software 126 may be stored in memory 130 for execution on processor 122 to generate super-alarm triggers 128 that are output to patient care professionals. The system 120 may take input from a plurality ports 124 connected to one or more patient monitoring devices. The inputted data from ports 124 may comprise sensor data of one or more physiological characteristics or traits, such as systolic arterial blood pressure, heart rate, blood oxygen saturation ($SpO_2$), asystole, ventricular tachycardia (v-tach), ventricular fibrillation (v-fib), temperature, etc.

Experimental Results

The ultimate evaluation of super-alarm is based on its online performance. There are four parameters that will determine the content of a super-alarm set. They include the length of the window (Win), value of the support (Sup), whether or not closed itemset filtering is enabled (Cls), and whether or not occurrence frequency encoding is used (Occ). Therefore, offline analysis is used to investigate: 1) what parameters/interactions the super-alarm algorithm is sensitive to; and 2) the optimal combination of algorithm parameters.

Figure 6A:
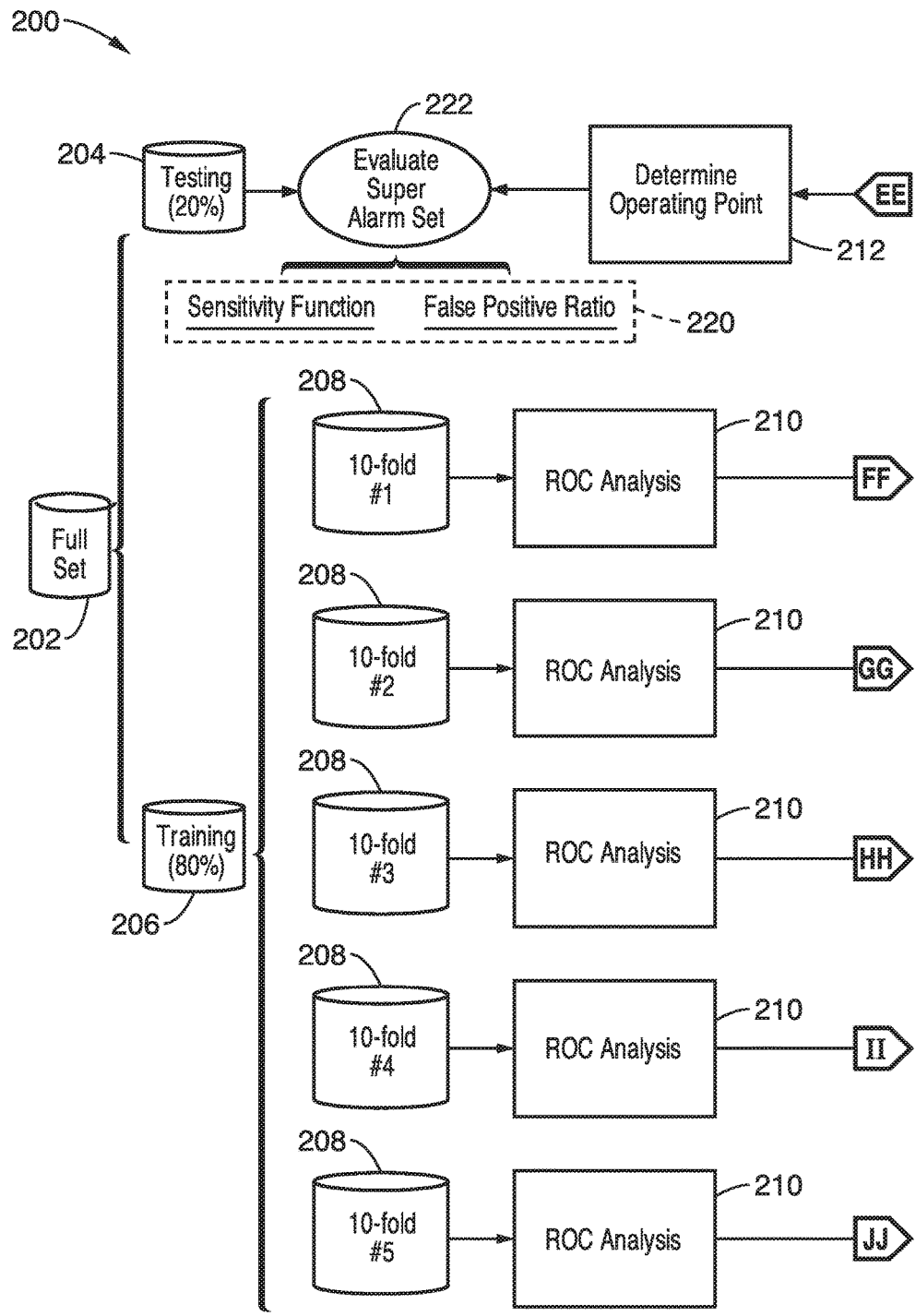
FIGS. 6A and 6B show a schematic diagram of a test setup for evaluation the methods of FIGS. 1A through 5.
Figure 6B:
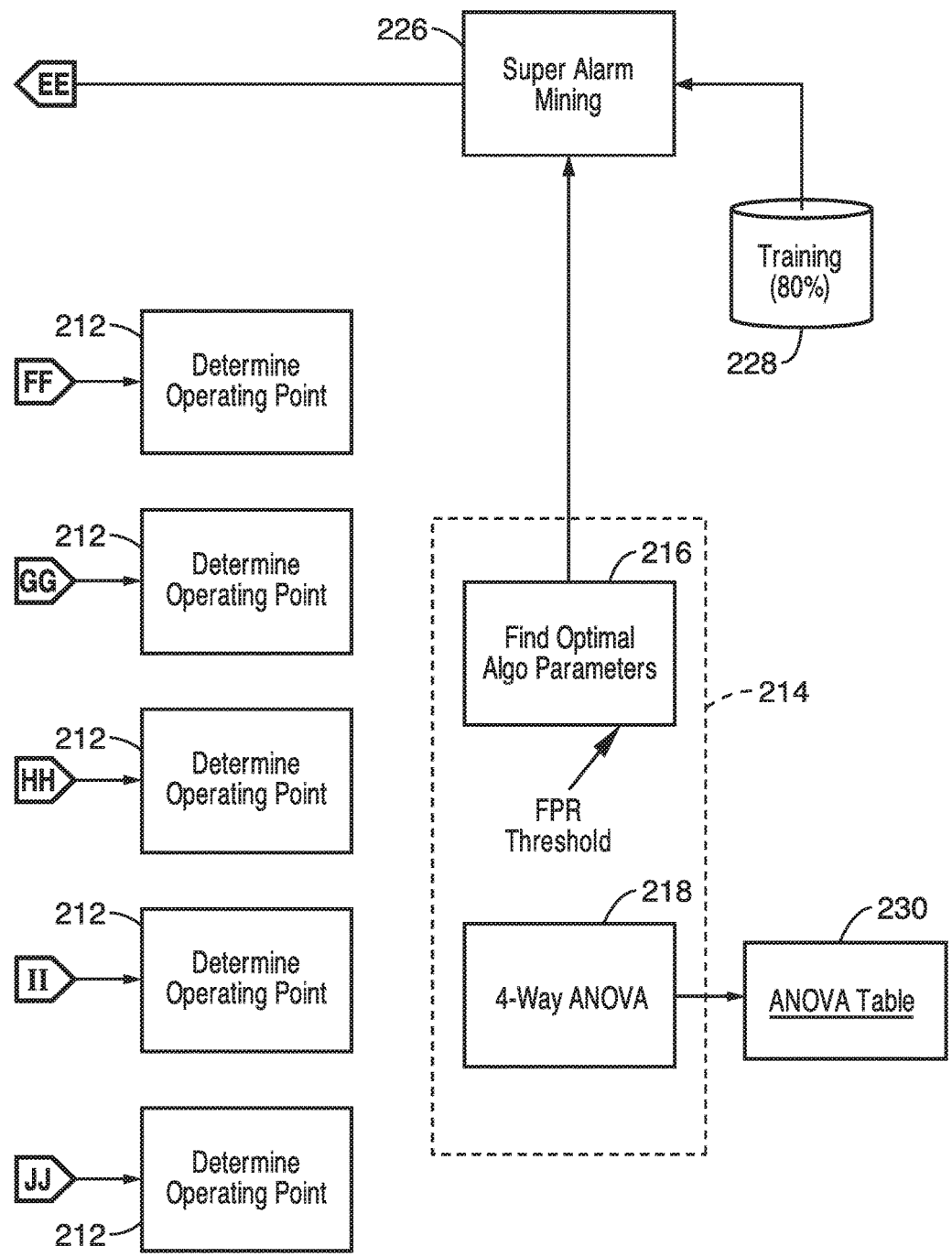

Referring now to the test setup 200 of the adopted alarm evaluation protocol illustrated in FIGS. 6A and 6B, two independent data sets are created from the full set 202. Alarms 204 from a randomly selected 20% of code blue patients and 20% of control patients are first reserved for online testing. Then multiple random copies of a 10-fold cross-validation (CV) data set 208 are generated using the alarms 206 from remaining 80% of patients for offline analysis. Each copy is generated by first randomly permuting the array of study subject identifiers of the remaining 80% of both code blue and control patients and then distributing the patients into 10 folds sequentially according to the permuted study subject identifiers. As shown in FIGS. 6A and 6B, more than one copy of 10-fold CV sets is needed because a N-way analysis of variance (ANOVA) will be used to assess the sensitivity of super-alarm to those algorithm parameters.

To obtain false positive rate at various steps in the offline analysis, alarms are sampled from control patients instead of using all alarms from them. This is done by randomly drawing one sample of alarms in each consecutive 4-hour window from the beginning of monitoring to the end. The number of alarms drawn for each sample obviously depends on the window length parameter (parameter $T_w$ in FIG. 1).

At step 210, a receiver operator characteristic (ROC) curve is generated for each 10-fold CV data set following the conventional cross-validation analysis. Given a selected set of algorithm parameters, the super-alarm mining algorithm is executed on the first nine folds of a 10-fold CV set to build a raw super-alarm set. By varying FPR threshold, the super-alarm patterns that have a FPR greater than the threshold can be trimmed, with the resulting super-alarm set on the remaining fold tested to count the number of true positive (TP) and the number of false positive (FP) hits. The process is repeated for each of the 10 folds and we accumulate the number of TP and FP hits at each threshold value. The true positive rate (TPR) is then simply calculated as the total TP hits across the 10 folds of data divided by the total number of code blue events and the false positive rate (FPR) is calculated as the total FP hits divided by the total number of control cases. A ROC curve can then be plotted by linking the FPR and TPR pairs obtained at each threshold. It should be noted that filtering the raw super-alarm set is part of the training process and hence the FPR of each super-alarm pattern is calculated based on the nine folds of training data. This process is executed for each copy of the 10-fold CV sets created at the beginning of the offline experiment.

Based on a ROC curve, an operating point 212 is picked by first specifying the maximally tolerated FPR (FPRmax) and then the operating point is determined at the location where the TPR is the maximized while the corresponding FPR is below the specified FPRmax. The TPR values 214 at this operating point can be collected from the ROC curves generated using different combinations of algorithm parameters for all copies of 10-fold CV sets. These TPR values are then used in a conventional full N-way ANOVA to assess the influence of the algorithm parameters on TPR.

In addition to the N-way ANOVA 218 and ANOVA table 230, the optimal combination of algorithm parameters are calculated at 216 for a given choice of FPRmax to be the one with maximal TPR for a given FPRmax averaged over all copies of 10-fold data sets.

The optimal algorithm combination 216 as found in offline analysis is used to conduct super-alarm mining 226 again by coalescing a 10-fold CV data set 228 into a full training data set 202. The raw super-alarm set thus identified is further filtered out using the average FPR threshold that determine the operating point for each of the copies of 10-fold CV data sets. This final super-alarm set is then applied to the reserved test data set for an online simulation study and obtain online performance metrics.

Two online metrics are designed. First, the super-alarm set 22 will be first applied following the method 100 detailed in FIG. 4 to all the alarms of code blue patients to calculate the online sensitivity (first half of block 220) that is a function of predictive horizon. This metric is defined as the percentage of code blue patients who have triggered super-alarm within a $T_p$—length prediction horizon that immediately precedes the event. It is expected that the sensitivity will increase as the prediction horizon is extended by increasing $T_p$. The second metric is calculated as the ratio of hourly number of false super-alarm triggers (second half of block 220) to that of the regular monitor alarms. Hence, the second metric quantifies the false positive aspect of a super-alarm set within the context of alarm load from current monitors.

Alarm data were extracted from a central repository of comprehensive data elements of bedside monitors in the UCLA Ronald Regan Medical Center. These bedside monitors were distributed across a neurosurgical ICU, cardiac observation unit, cardiothoracic ICU, coronary ICU, hematology and stem cell transplant unit, medical ICU, medical-surgical specialty unit, neuroscience and stoke unit, liver transplant unit, and transplant surgical ICU. Continuous waveform, vital signs at a 15-minute interval, and alarms are continuously archived into the repository using a commercial data acquisition system equipped with 200 data acquisition licenses. Hence, data from only up to 200 beds can be archived simultaneously. The data acquisition system determines data from which bed to be archived when a license becomes available. A list of code blue events from April 2010 to October 2011 was provided. Using this list, alarms for 223 code blue adult patients (age>18 years) were collected.

In addition, control patients were determined by applying the following inclusion and exclusion criteria to patients admitted between April 2010 and October 2011 who were not coded nor experienced an unplanned ICU transfer. The inclusion criteria are: 1) have the same APR DRG (All Patient Refined Diagnosis Related Group) or Medicare DRG; 2) the age is within 5 years; 3) have the same gender; 4) resided in the same unit during their stay. These criteria were applied to find as many as possible control patients per each code blue patient. The total number of control patients thus identified was 1768.

The results reported in this section are based on the following setup of the experiment conditions. Four levels of window length were assessed: 10 minutes, 30 minutes, 1 hour, and 2 hours. Four levels of minimum support value for mining the frequent itemset were used: 0.05, 0.10, 0.15, and 0.25. Closed itemset filtering and occurrence frequency encoding are two binary choices. Hence, there are 64 combinations of algorithm parameters in the N-way ANOVA. To obtain reliable results, five copies of 10-fold cross-validation data sets 208 were generated, which is equivalent to testing algorithm combination using five random cross-validation experiments. This is enough to provide samples needed for a 4-way ANOVA 218, while keeping the computational cost minimal. The performance of the super-alarm set 222 is determined by its maximal true positive rate while satisfying a user-specified maximal false positive rate, which is specified as 0.02, 0.05, 0.10, and 0.15. Therefore, a four 4-way ANOVA analysis was conducted to obtain the following results.

The total number of alarms was 882,414 for 223 code blue patients and 3,921,323 for 1768 control patients. The average monitoring time was 398.5±524.0 hours for the code blue patients and 249.5±345.4 hours for control patients. There were 33 patients who had more than one code blue call. Only alarms from the first code blue call were selected for analysis.

The distributions of alarms for code blue and controls patients across the four alarms levels are: [2.18%, 11.40%, 70.16%, and 16.23%] and [1.50%, 10.75%, 69.56%, 18.19%], respectively. This shows that crisis alarms account for less than 2.5% of all levels of alarms for code blue and less than 2.0% for control patients. On the other hand, patient advisory alarm is a dominant level. Average age is 61.1±16.9 years for code blue patients and 63.6±14.8 years for controls. 58% of code blue patients and 66% of controls were male. Cardiac and respiratory arrests accounted for 74% and 22% of cases, respectively. The majority of code blue events occurred in ICUs (68%) with 23% code blue events occurring in non-ICU units, and 9% in other facilities including OR and interventional suits. On the other hand, 67% controls were ICU patients and 33% of them were from non-ICU units.

Figure 7:
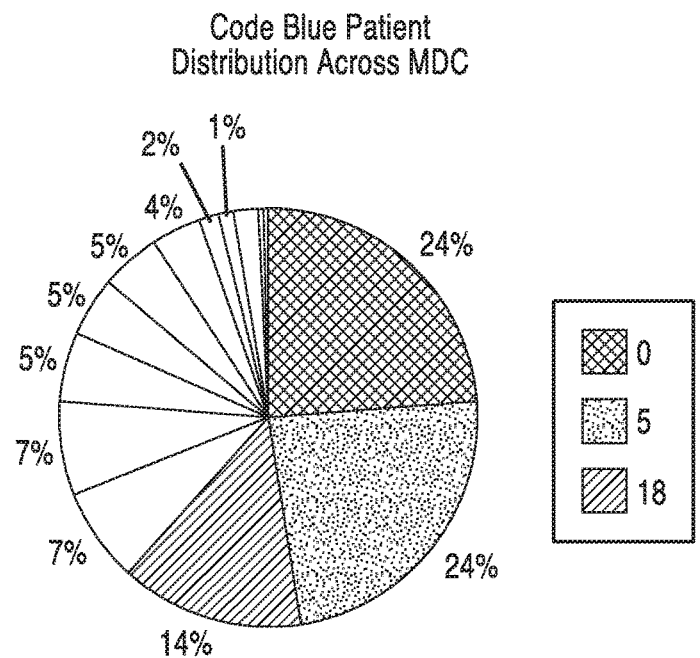
FIG. 7 is a graph showing distribution of the major diagnostic category for 223 code blue events across 26 categories (0~25).
Figure 8:
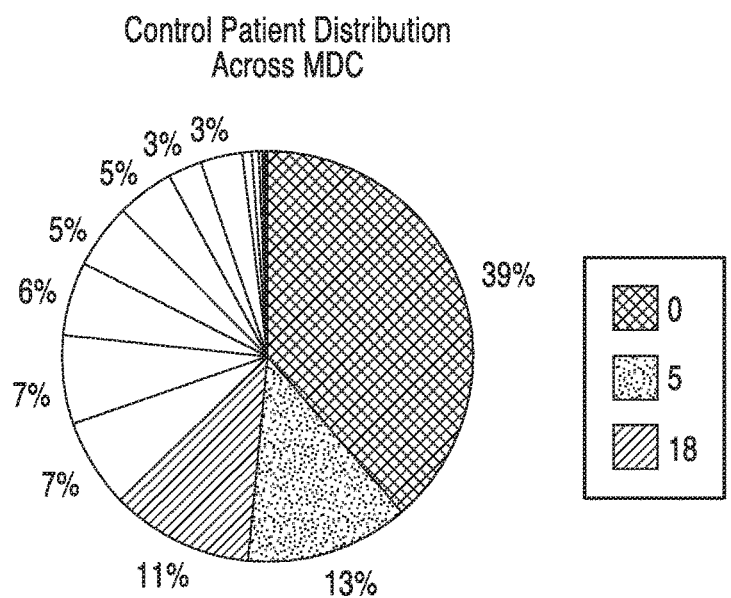
FIG. 8 is a graph showing distribution of the major diagnostic category for 1768 control patients across 26 categories (0~25).

The distribution of code blue events and control patients across 26 different major diagnostic codes is shown in FIG. 7 and FIG. 8, respectively. MDC 0 is a code used to designate a number of different diagnosis and procedure situations that are transplant-related. This code accounts for the biggest number of code blue patients. The second, the third, the fourth largest MDC code for code blue are MDC 5, MDC 18, and MDC 4, which are related to circulatory system, infectious situations, and respiratory system respectively. For control patients, the largest cluster is also MDC 0 followed by MDC 5, 18, and 4.

Figure 9:
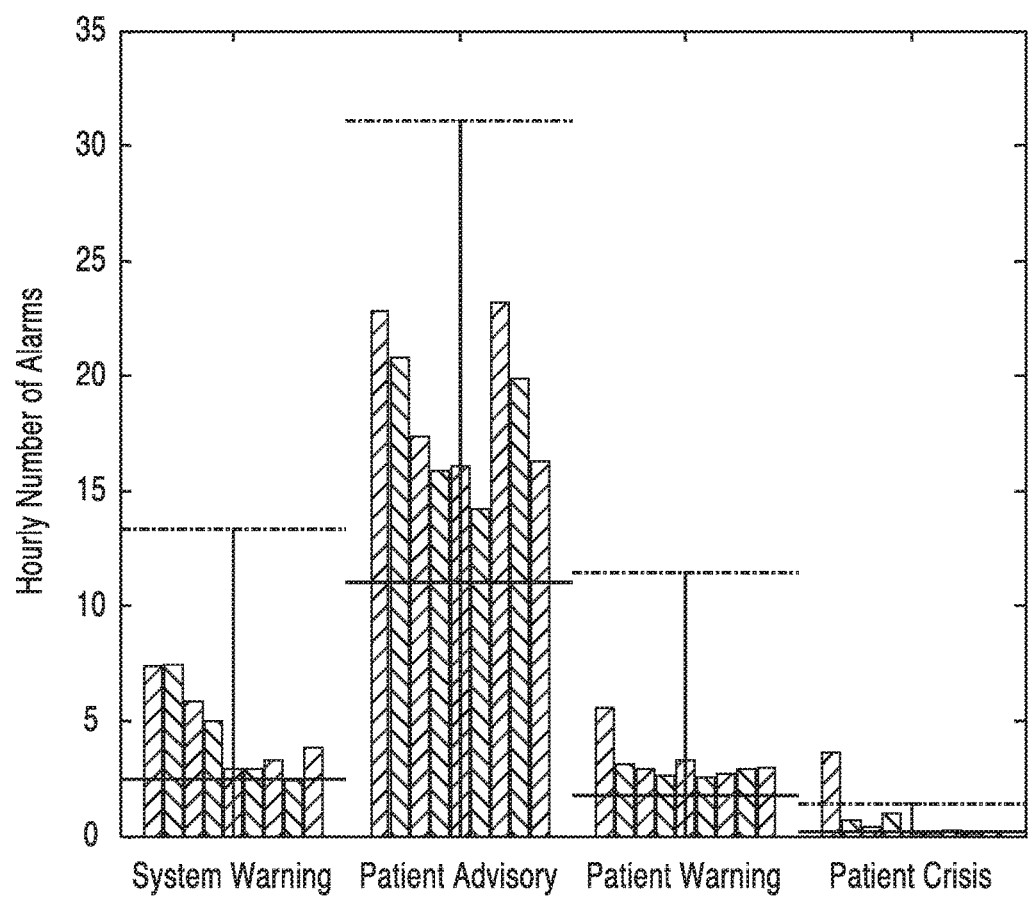
FIG. 9 is a graph showing average hourly number of alarms of code blue patients and controls grouped by the four levels of alarms as built in bedside monitors. Each of the nine bars represents the average number of alarms of code blue patients within nine consecutive 1-hour periods preceding the code blue events.

The four solid lines in FIG. 9 display the average hourly number of alarms per each of the four alarm levels for control patients (using 10 randomly selected 1-hour windows). The nine bars display the average hourly number of alarms for code blue patients at 9 different time windows prior to the event. These 9 windows are all one-hour long, non-overlapped and placed consecutively prior to the event starting at the time of the code blue events. FIG. 9 shows that the code blue patients have a larger number of alarms and that the number of alarms is the largest within the last hour leading to the code blue event except for the patient advisory alarms.

Table 2 lists the p values of 15 parameters and their interactions from the 4-way ANOVA, showing the of the influence of four algorithm parameters and their interactions on super-alarm performance, which was calculated as the maximal true positive rate obtained for a given maximal false positive rate (FPR). These parameters are window length (Win), minimum support value (Sup), closed itemset filtering (Cls), and occurrence frequency encoding (Occ). It can be clearly seen that window length (Win), support values (Sup), and their interaction are the three most significant factors. On the other hand, occurrence frequency encoding and closed itemset filtering have less influence on the performance of super-alarm as they only affect performance under certain choice of FPR thresholds and have larger p values.

Based on the offline evaluation results, we determine the optimal algorithm parameters for a given FPR threshold and then use the full training data to obtain the super-alarm set. Table 3 lists the optimal parameters for each choice of FPR threshold, the total number of super-alarm patterns, the total number of super-alarms per each pattern length, and the average sensitivity obtained at the specified FPR threshold. For example, a FPR threshold of 0.15 resulted in the largest super-alarm set which also contains the longest super-alarm pattern (n=6) and highest sensitivity (0.65±0.02). Interestingly, a FPR threshold of 0.1, instead of 0.02, resulted in the smallest super-alarm set, which can be attributed to a large support value used in the super-alarm mining. However, a higher average sensitivity is always obtained at a higher FPR threshold, irrespective of the size of the super-alarm set. Furthermore, neither large window length nor large support value has been preferred as optimal parameters to be used for mining the super-alarms.

As an example of a super-alarm set, Table 4 lists the full super-alarm set as found using a FPR threshold of 0.1 under the algorithm parameters listed in the 3rd row of Table 3. There were 29 super-alarm patterns including 7 patterns consisting of one code, 19 patterns consisting of two codes, and 3 patterns consisting of 3 codes. There were no patterns found that consist of more than three codes.

Figure 10:
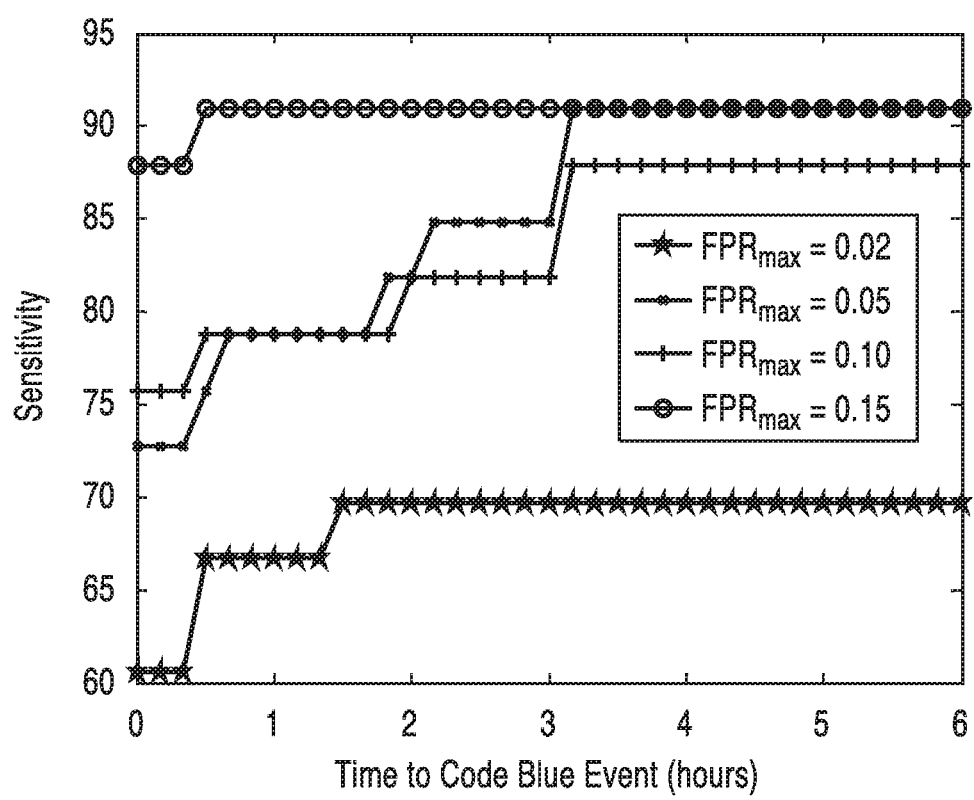
FIG. 10 is a graph showing sensitivity curves of four super-alarm sets obtained using the optimal algorithm parameters under four different false positive ratio thresholds.

FIG. 10 displays the sensitivity functions using the four super-alarm sets determined using the whole training data set under the optimal parameters as determined in the offline analysis. In addition, Table 5 lists the ratio of the number of false positive super-alarms to that of regular monitor alarms and the sensitivity obtained at prediction horizons of 30 minutes, 1 hour, and 2 hours. It can be seen from these results that a higher FPR threshold leads to a larger sensitivity, especially at a shorter prediction horizon but also a larger false positive ratio for the super-alarm set. However, the largest super-alarm set obtained under a FPR threshold of 0.15 achieves a sensitivity of 90.9% at detecting code blue one hour ahead. Even with this largest super-alarm set, the number of false alarms it would raise for control patients only accounts for 11.2% of regular monitor alarms.

In summary, the systems and methods of the present invention can predict clinical end-points such as code blue, and that by doing so may provide innovative strategies of alarm management to alleviate the alarm fatigue from excessive number of false positive alarms. In particular alarm mining approach is detailed based on finding frequent combinations of individual alarms specific to predict code blue events.

It will be appreciated that the classic Apriori algorithm was used to find the frequent itemsets. A general requirement of this algorithm is that a constant minimum support threshold is used. It is also appreciated that a smaller minimum support threshold as the length of a potential super-alarm pattern increases so that more specific and hence longer super-alarm patterns will not be missed. Alternative association rule mining algorithms that are more computationally efficient may also be employed in the method of the present invention to handle a larger data set.

Furthermore, the order of the appearance of individual alarms when composing a super-alarm pattern may also be factored in the method of the present invention to increase further the specificity of super-alarm. Several alternative potential approaches to incorporate the order of alarms include: hidden Markov models, which have been demonstrated with better performance than itemset-based approach in predicting faults, and sequential alarm pattern mining approaches.

The alarm mining methods of the present invention are also complementary to existing approaches that are based on robust signal analysis and pattern recognition techniques to improve patient monitoring. One potential way of integrating these approaches is to utilize the alarm mining as a framework to include outputs from signal analysis and pattern recognitions of physiological signals as alarms. This is because the methods of the present invention are not limited to alarms from monitors. Indeed, there are known predictors of cardiac arrest that can be derived from advanced ECG and rhythm analysis beyond what is done by conventional monitors.

It is known that less critical alarms account for majority of all received alarms (97.82% and 98.50% for code blue and control patients, respectively in our data set) and they are prone to being affected by noise and artifacts. As such, they are more likely to be ignored by care givers. Hence, the super-alarm methods of the present invention have significant potential to provide evidence-based indication that combinations of even less critical alarms may be predictive of impending or ongoing patient deteriorations and therefore demand attention that are currently mandated for critical alarms. Such a system may mitigate the problem of alarm fatigue while minimizing the risk of missing important precursory patterns in the sequence of alarms for deteriorating patients.

Embodiments of the present invention may be described with reference to flowchart illustrations of methods and systems according to embodiments of the invention, and/or algorithms, formulae, or other computational depictions, which may also be implemented as computer program products. In this regard, each block or step of a flowchart, and combinations of blocks (and/or steps) in a flowchart, algorithm, formula, or computational depiction can be implemented by various means, such as hardware, firmware, and/or software including one or more computer program instructions embodied in computer-readable program code logic. As will be appreciated, any such computer program instructions may be loaded onto a computer, including without limitation a general purpose computer or special purpose computer, or other programmable processing apparatus to produce a machine, such that the computer program instructions which execute on the computer or other programmable processing apparatus create means for implementing the functions specified in the block(s) of the flowchart(s).

Accordingly, blocks of the flowcharts, algorithms, formulae, or computational depictions support combinations of means for performing the specified functions, combinations of steps for performing the specified functions, and computer program instructions, such as embodied in computer-readable program code logic means, for performing the specified functions. It will also be understood that each block of the flowchart illustrations, algorithms, formulae, or computational depictions and combinations thereof described herein, can be implemented by special purpose hardware-based computer systems which perform the specified functions or steps, or combinations of special purpose hardware and computer-readable program code logic means.

Furthermore, these computer program instructions, such as embodied in computer-readable program code logic, may also be stored in a computer-readable memory that can direct a computer or other programmable processing apparatus to function in a particular manner, such that the instructions stored in the computer-readable memory produce an article of manufacture including instruction means which implement the function specified in the block(s) of the flowchart(s). The computer program instructions may also be loaded onto a computer or other programmable processing apparatus to cause a series of operational steps to be performed on the computer or other programmable processing apparatus to produce a computer-implemented process such that the instructions which execute on the computer or other programmable processing apparatus provide steps for implementing the functions specified in the block(s) of the flowchart(s), algorithm(s), formula(e), or computational depiction(s).

From the discussion above it will be appreciated that the invention can be embodied in various ways, including the following:

1. A system for monitoring data associated with a plurality of physiological characteristics of a patient, comprising: a processor configured for receiving input from a plurality of independent physiological data streams from one or more monitoring devices; wherein each of the physiological data streams comprises an individual raw alarm associated with the physiological data within the stream; and programming executable on the processor for: reading the input physiological data streams; comparing the input data stream against a set of super-alarm patterns associated with the plurality of physiological conditions; the super-alarm patterns comprising data relating to a combination of at least two individual raw alarms from independent physiological data streams that co-occur within a temporal window; and triggering an alarm if a combination of the input physiological data matches at least a portion of a generated super-alarm pattern.

2. A system as in any of the preceding embodiments, wherein the triggered alarm is predictive of an adverse event associated with the physiological characteristics of a patient.

3. A system as in any of the preceding embodiments, wherein the triggered alarm is predictive of a code-blue event.

4. A system as in any of the preceding embodiments, wherein the set of super-alarm patterns are generated by: acquiring physiological monitoring case data from a comprising raw alarm data plurality of patient cases; detecting super-alarm patterns occurring above a specified frequency within a window of time directly preceding an adverse event within each of the cases.

5. A system as in any of the preceding embodiments, wherein the set of super-alarm patterns are generated by: acquiring physiological monitoring control data comprising raw alarm data from a plurality of control patients that are not coded; and discretizing a value field for raw alarms based on the case data and the control data.

6. A system as in any of the preceding embodiments, wherein raw control alarms and case alarms that co-occur within a specified time window are pre-processed to generate an output of an array of alarm codes, each of which identifies an individual raw alarm.

7. A system as in any of the preceding embodiments, wherein discretizing a value field comprises dividing an alarm with a value code into sub-codes.

8. A system as in any of the preceding embodiments, wherein the control data is used to filter out super-alarm patterns identified for adverse event patients that have also occurred above a specified frequently for control patients.

9. A system as in any of the preceding embodiments: wherein a super-alarm pattern is excluded from inclusion within the super-alarm pattern set if the super-alarm pattern has false positive rate (FPR) is greater than a predetermined threshold; wherein the false positive rate (FPR) of the super-alarm pattern is a function of the acquired control data.

10. A system as in any of the preceding embodiments, wherein the set of super-alarm patterns are generated by: generating encoding schema; wherein encoding schema used to encode alarm codes for case alarms and control alarms.

11. A system as in any of the preceding embodiments, further comprising: generating encoding schema as a function of an occurrence frequency for each alarm code.

12. A system as in any of the preceding embodiments, wherein the set of super-alarm patterns are generated by: applying closed-set filtering to remove super-alarm patterns that are included as a subset of a larger super-alarm pattern.

13. A system for generating a set of alarm patterns associated with a plurality of physiological characteristics of a patient, the alarm patterns being predictive of an adverse event associated with the physiological characteristics of a patient, comprising: a database comprising physiological monitoring case data comprising raw alarm data from a plurality of patient cases and a plurality of control patients that are not coded; a processor; programming executable on the processor for: evaluating raw alarm data from a plurality of patient cases and a plurality of control patients; and generating a set of super-alarm patterns associated with the plurality of physiological conditions; the super-alarm patterns comprising data relating to a combination of at least two individual raw alarms from independent physiological data readings of the patient.

14. A system as in any of the preceding embodiments, wherein generating a set of super-alarm patterns comprises: detecting super-alarm patterns occurring above a specified frequency within a window of time directly preceding an adverse event within each of the cases.

15. A system as in any of the preceding embodiments, wherein generating a set of super-alarm patterns comprises: discretizing a value field for raw alarms based on the case data and the control data.

16. A system as in any of the preceding embodiments, wherein raw control alarms and case alarms that co-occur within a specified time window are pre-processed to generate an output of an array of alarm codes, each of which identifies an individual raw alarm.

17. A system as in any of the preceding embodiments, wherein discretizing a value field comprises dividing an alarm with a value code into sub-codes.

18. A system as in any of the preceding embodiments, wherein the control data is used to filter out super-alarm patterns identified for adverse event patients that have also occurred above a specified frequently for control patients.

19. A system as in any of the preceding embodiments: wherein a super-alarm pattern is excluded from inclusion within the super-alarm pattern set if the super-alarm pattern has a false positive rate (FPR) greater than a predetermined threshold; wherein the false positive rate (FPR) of the super-alarm pattern is a function of the acquired control data.

20. A system as in any of the preceding embodiments, wherein generating a set of super-alarm patterns further comprises: generating encoding schema; wherein encoding schema is used to encode alarm codes for case alarms and control alarms.

21. A system as in any of the preceding embodiments, further comprising: generating encoding schema as a function of an occurrence frequency for each alarm code.

22. A system as in any of the preceding embodiments, wherein generating a set of super-alarm patterns further comprises: applying closed-set filtering to remove super-alarm patterns that are included as a subset of a larger super-alarm pattern.

23. A monitor for predicting an adverse event associated with the physiological characteristics of a patient, comprising: one or more monitor inputs configured for receiving input from a plurality of independent physiological data streams generated from one or more monitoring devices; wherein each of the physiological data streams comprises an individual raw alarm associated with the physiological data within the stream; a processor coupled to the one or more monitor inputs; and programming executable on the processor for: reading the input physiological data streams; comparing the input data stream against a set of super-alarm patterns associated with the plurality of physiological conditions; the super-alarm patterns comprising data relating to a combination of at least two individual raw alarms from independent physiological data streams that co-occur within a temporal window; and triggering an alarm if a combination of the input physiological data matches at least a portion of a generated super-alarm pattern 24. A monitor as in any of the preceding embodiments, wherein the triggered alarm is predictive of a code-blue event.

25. A monitor as in any of the preceding embodiments, wherein the set of super-alarm patterns are generated by: acquiring physiological monitoring case data from a comprising raw alarm data plurality of patient cases; detecting super-alarm patterns occurring within a window of time directly preceding an adverse event within each of the cases.

26. A monitor as in any of the preceding embodiments, wherein the set of super-alarm patterns are generated by: acquiring physiological monitoring control data comprising raw alarm data from a plurality of control patients that are not coded; and discretizing a value field for raw alarms based on the case data and the control data.

27. A monitor as in any of the preceding embodiments, wherein raw control alarms and case alarms that co-occur within a specified time window are pre-processed to generate an output of an array of alarm codes, each of which identifies an individual raw alarm.

28. A monitor as in any of the preceding embodiments, wherein discretizing a value field comprises dividing an alarm with a value code into sub-codes.

29. A monitor as in any of the preceding embodiments, wherein the control data is used to filter out super-alarm patterns identified for adverse event patients that have also occurred above a specified frequently for control patients.

30. A monitor as in any of the preceding embodiments: wherein a super-alarm pattern is excluded from inclusion within the super-alarm pattern set if the super-alarm pattern has a false positive rate (FPR) greater than a predetermined threshold; wherein the false positive rate (FPR) of the super-alarm pattern is a function of the acquired control data.

31. A monitor as in any of the preceding embodiments, wherein the set of super-alarm patterns are generated by: generating encoding schema; wherein encoding schema used to encode alarm codes for case alarms and control alarms.

32. A monitor as in any of the preceding embodiments, further comprising: generating encoding schema as a function of an occurrence frequency for each alarm code.

33. A monitor as in any of the preceding embodiments, wherein the set of super-alarm patterns are generated by: applying closed-set filtering to remove super-alarm patterns that are included as a subset of a larger super-alarm pattern.

Although the description above contains many details, these should not be construed as limiting the scope of the invention but as merely providing illustrations of some of the presently preferred embodiments of this invention. Therefore, it will be appreciated that the scope of the present invention fully encompasses other embodiments which may become obvious to those skilled in the art, and that the scope of the present invention is accordingly to be limited by nothing other than the appended claims, in which reference to an element in the singular is not intended to mean "one and only one" unless explicitly so stated, but rather "one or more." All structural, chemical, and functional equivalents to the elements of the above-described preferred embodiment that are known to those of ordinary skill in the art are expressly incorporated herein by reference and are intended to be encompassed by the present claims. Moreover, it is not necessary for a device or method to address each and every problem sought to be solved by the present invention, for it to be encompassed by the present claims. Furthermore, no element, component, or method step in the present disclosure is intended to be dedicated to the public regardless of whether the element, component, or method step is explicitly recited in the claims. No claim element herein is to be construed under the provisions of 35 U.S.C. 112, sixth paragraph, unless the element is expressly recited using the phrase "means for."

TABLE 1

Composition Of Monitor Alarms Using Four Example Alarms

| Alarm Code | Label | Level | Polarity | Value | Timestamp |
|---|---|---|---|---|---|
| 90 | ART1 S | Patient warning | LO | 80 | 6/23/2011 14:50:11 |
| | Systolic arterial blood pressure at port #1 crosses the preset alarm lower bound at a value of 80 mmHg at the specified time point. | | | | |
| 89 | ART1 S | Patient warning | HI | 180 | 6/2/2011 4:30:11 |
| | Systolic arterial blood pressure at port #1 crosses the preset alarm upper bound at a value of 180 mmHg at the specified time point. | | | | |
| 1 | Asystole | Crisis | N/A | N/A | 6/23/2011 5:20:10 |
| | An asystole alarm is trigged at the specified time point | | | | |
| 190 | NBP S | Patient warning | HI | 160 | 6/23/2011 11:50:11 |
| | Noninvasive systolic arterial blood pressure crosses the preset alarm upper bound at a value of 160 mmHg at the specified time point | | | | |

TABLE 2

P Values From Conducting A 4-Way Analysis Of Variance (ANOVA)

| Parameters & Interactions | FPR = 0.02 | FPR = 0.05 | FPR = 0.10 | FPR = 0.15 |
|---|---|---|---|---|
| Win | 0.006 | 0.000 | 0.000 | 0.000 |
| Sup | 0.000 | 0.000 | 0.000 | 0.001 |
| Occ | 0.633 | 0.310 | 0.017 | 0.487 |
| Cls | 0.895 | 0.049 | 0.016 | 0.535 |
| Win&Sup | 0.000 | 0.000 | 0.000 | 0.000 |
| Win&Occ | 0.822 | 0.369 | 0.740 | 0.539 |
| Win&Cls | 0.698 | 0.195 | 0.005 | 0.100 |
| Sup&Occ | 0.297 | 0.901 | 0.118 | 0.614 |
| Sup&Cls | 0.013 | 0.000 | 0.013 | 0.141 |
| Cls&Occ | 0.925 | 0.286 | 0.239 | 0.350 |
| Win&Sup&Occ | 0.851 | 0.858 | 0.900 | 0.024 |
| Win&Sup&Cls | 0.596 | 0.063 | 0.048 | 0.001 |
| Win&Occ&Cls | 0.589 | 0.262 | 0.883 | 0.652 |
| Sup&Cls&Occ | 0.956 | 0.799 | 0.540 | 0.015 |
| Win&Sup&Occ&Cls | 0.987 | 0.710 | 0.934 | 0.398 |

TABLE 3

List Of The Optimal Algorithm Parameters

| False positive rate threshold | Window Length (minutes) | Support value | Closed set filtering | Occurrence frequency encoding | # of Super-alarm patterns | # of Super-alarm patterns per length | Sensitivity (mean ± sd) |
|---|---|---|---|---|---|---|---|
| 0.02 | 30 | 0.05 | True | True | 143 | [1,77,40,25] | 0.44 ± 0.02 |
| 0.05 | 10 | 0.05 | False | False | 97 | [6,59,28,4] | 0.53 ± 0.01 |
| 0.10 | 30 | 0.10 | False | False | 29 | [7,19,3] | 0.63 ± 0.04 |
| 0.15 | 60 | 0.05 | False | True | 658 | [0,150,335,148,24,1] | 0.65 ± 0.02 |

TABLE 4

List Of The Smallest Super-Alarms Set Found

| Length of Patterns | Super-alarm Patterns |
|---|---|
| 1 | ASYSTOLE |
| | VFIB/VTAC |
| | V BRADY |
| | PAUSE |
| | ACC VENT |
| | ART1 M LO28.5< <37.5 |
| | ART1 M LO37.5< <52.5 |
| 2 | ASYSTOLE & VFIB/VTAC |
| | ASYSTOLE & BRADY |
| | ASYSTOLE & V TACH |
| | ASYSTOLE & HR LO33.5< <75.0 |
| | ASYSTOLE & SPO2 LO83.5< <93.5 |
| | VFIB/VTAC & V TACH |
| | VFIB/VTAC & SPO2 LO83.5< <93.5 |
| | BRADY & V TACH |
| | BRADY & SPO2 LO66.5< <83.5 |
| | BRADY & SPO2 LO83.5< <93.5 |
| | V TACH & VT >2 |
| | V TACH & PVC<43.5 |
| | V TACH & SPO2 LO66.5< <83.5 |
| | V TACH & SPO2 LO83.5< <93.5 |
| | HR LO33.5< <75.0 & SPO2 LO66.5< <83.5 |
| | HR LO33.5< <75.0 & SPO2 LO83.5< <93.5 |
| | SPO2 LO<66.5 & SPO2 LO66.5< <83.5 |
| | SPO2 LO<66.5 & SPO2 LO83.5< <93.5 |
| | ART1 D LO30.5< <78.0 & ART1 S LO40.0< <70.5 |
| 3 | ASYSTOLE & VFIB/VTAC & V TACH |
| | V TACH & SPO2 LO66.5< <83.5 & SPO2 LO83.5< <93.5 |
| | SPO2 LO<66.5 & SPO2 LO66.5< <83.5 & SPO2 LO83.5< <93.5 |

TABLE 5

List Of Online Performance Metrics For Four Super-Alarm Sets

| False positive rate threshold | Sensitivity ½-hour | Sensitivity 1-hour | Sensitivity 2-hour | False positive ratio |
|---|---|---|---|---|
| 0.02 | 60.6% | 66.7% | 69.7% | 2.2% ± 4.3% |
| 0.05 | 72.7% | 78.8% | 81.8% | 4.7% ± 7.0% |
| 0.10 | 75.8% | 78.8% | 78.8% | 7.4% ± 9.0% |
| 0.15 | 87.9% | 90.9% | 90.9% | 11.2% ± 12.5% |

What is claimed is:

1. A system for monitoring data associated with a plurality of physiological characteristics of a patient, comprising:
   a processor configured for receiving input from a plurality of independent physiological data streams from one or more monitoring devices;
   wherein each of the physiological data streams comprises an individual raw alarm associated with the physiological data within the stream; and
   programming executable on the processor for:
      reading the input physiological data streams;

comparing the input data stream against a set of predictive super-alarm patterns associated with the plurality of physiological conditions;

the predictive super-alarm patterns comprising a temporal window data acquired from a combination of at least two individual independent physiological data streams that co-occur within the temporal window; and triggering an alarm if a combination of the input physiological data matches at least a portion of a generated super-alarm pattern;

wherein the triggered alarm is predictive of an adverse event associated with the physiological characteristics of a patient.

2. A system as recited in claim 1, wherein the at least two individual independent physiological data streams comprise raw alarm data.

3. A system as recited in claim 1, wherein the triggered alarm is predictive of a code-blue event.

4. A system as recited in claim 1, wherein the set of predictive super-alarm patterns are generated by:

acquiring physiological monitoring case data from data acquired from a plurality of patient cases; and detecting super-alarm patterns occurring within a temporal window preceding an adverse event within each of the patient cases;

wherein the detected adverse event within the case data is correlative to the adverse event associated with the physiological characteristics of the patient.

5. A system as recited in claim 4, wherein the set of predictive super-alarm patterns are generated by:

acquiring physiological monitoring control data comprising raw alarm data from a plurality of control patients, the control patient alarm data comprising super-alarm patterns not occurring within the temporal window of an adverse event; and discretizing a value field for raw alarms based on the case data and the control data.

6. A system as recited in claim 5, wherein raw control alarms and case alarms that co-occur within a specified time window are pre-processed to generate an output of an array of alarm codes, each of which identifies an individual raw alarm.

7. A system as recited in claim 5, wherein discretizing a value field comprises dividing an alarm with a value code into sub-codes.

8. A system as recited in claim 5, wherein the control data is used to filter out non-predictive super-alarm patterns identified for adverse event patients that have also occurred above a specified frequently for control patients.

9. A system as recited in claim 5:

wherein a super-alarm pattern is excluded from inclusion within the predictive super-alarm pattern set if the super-alarm pattern has false positive rate (FPR) greater than a predetermined threshold; and wherein the false positive rate (FPR) of the super-alarm pattern is a function of the acquired control data.

10. A system as recited in claim 5, wherein the set of predictive super-alarm patterns are generated by:

generating encoding schema;

wherein encoding schema used to encode alarm codes for case alarms and control alarms.

11. A system as recited in claim 10, further comprising: generating encoding schema as a function of an occurrence frequency for each alarm code.

12. A system as recited in claim 1, wherein the set of predictive super-alarm patterns are generated by:

applying closed-set filtering to remove predictive super-alarm patterns that are included as a subset of a larger predictive super-alarm pattern.

13. A system for generating a set of predictive alarm patterns associated with a plurality of physiological characteristics of a patient, the predictive alarm patterns being predictive of an adverse event associated with the physiological characteristics of a patient, comprising:

a database comprising physiological monitoring case data acquired from raw physiological data from a plurality of patient cases and a plurality of control patients that are not coded with respect to the adverse event;

a processor;

programming executable on the processor for:

evaluating raw physiological data from a plurality of patient cases and a plurality of control patients; and generating a set of predictive super-alarm patterns associated with the plurality of physiological conditions;

the predictive super-alarm patterns comprising a temporal window of data acquired from a combination of at least two individual encoded independent physiological data streams that co-occur within the temporal window.

14. A system as recited in claim 13, wherein generating a set of predictive super-alarm patterns comprises:

detecting super-alarm patterns occurring within a temporal window preceding an adverse event within each of the patient cases;

wherein the detected adverse event within the case data is correlative to the adverse event associated with the physiological characteristics of the patient.

15. A system as recited in claim 13, wherein the physiological data from the plurality of control patients comprises super-alarm patterns not occurring within the temporal window of an adverse event, and wherein generating a set of super-alarm patterns comprises:

discretizing a value field for the physiological data based on the case data and the control data.

16. A system as recited in claim 15, wherein discretizing a value field comprises dividing an alarm with a value code into sub-codes.

17. A system as recited in claim 13, wherein raw control alarms and case alarms that co-occur within a specified time window are pre-processed to generate an output of an array of alarm codes, each of which identifies an individual raw alarm.

18. A system as recited in claim 13, wherein the control data is used to filter out non-predictive super-alarm patterns identified for adverse event patients that have also occurred above a specified frequently for control patients.

19. A system as recited in claim 13:

wherein a super-alarm pattern is excluded from inclusion within the predictive super-alarm pattern set if the super-alarm pattern has a false positive rate (FPR) greater than a predetermined threshold;

wherein the false positive rate (FPR) of the super-alarm pattern is a function of the acquired control data.

20. A system as recited in claim 13, wherein generating a set of predictive super-alarm patterns further comprises:

generating encoding schema;

wherein encoding schema is used to encode alarm codes for case alarms and control alarms.

21. A system as recited in claim 20, further comprising: generating encoding schema as a function of an occurrence frequency for each alarm code.

22. A system as recited in claim 13, wherein generating a set of predictive super-alarm patterns further comprises:
applying closed-set filtering to remove predictive super-alarm patterns that are included as a subset of a larger predictive super-alarm pattern.

23. A monitor for predicting an adverse event associated with the physiological characteristics of a patient, comprising:
one or more monitor inputs configured for receiving input from a plurality of independent physiological data streams generated from one or more monitoring devices;
wherein each of the physiological data streams comprises an individual raw alarm associated with the physiological data within the stream;
a processor coupled to the one or more monitor inputs; and
programming executable on the processor for:
reading the input physiological data streams;
comparing the input data stream against a set of predictive super-alarm patterns associated with the plurality of physiological conditions;
the predictive super-alarm patterns comprising a temporal window of data acquired from a combination of at least two individual encoded raw alarms from independent physiological data streams that co-occur within the temporal window; and
triggering an alarm if a combination of the input physiological data matches at least a portion of a generated predictive super-alarm pattern;
wherein the triggered alarm is predictive of an adverse event associated with the physiological characteristics of a patient.

* * * * *